United States Patent [19]

Saravia et al.

[11] Patent Number: 6,106,494

[45] Date of Patent: Aug. 22, 2000

[54] SELF-CONTAINED FLUID MANAGEMENT PUMP SYSTEM FOR SURGICAL PROCEDURES

[75] Inventors: Heber Saravia, San Francisco; Jens Voges, Palo Alto, both of Calif.

[73] Assignee: Stryker Corporation, Kalamazoo, Mich.

[21] Appl. No.: 09/272,264

[22] Filed: Mar. 19, 1999

[51] Int. Cl.[7] .................................................. A61M 1/00
[52] U.S. Cl. ............................................. 604/35; 604/151
[58] Field of Search .................................. 604/30, 65–67, 604/19, 131, 31, 36, 151, 135; 128/DIG. 13, DIG. 14

[56] References Cited

U.S. PATENT DOCUMENTS

| | | |
|---|---|---|
| 5,433,588 | 7/1995 | Monk et al. . |
| 5,613,954 | 3/1997 | Nelson et al. . |
| 5,810,770 | 9/1998 | Chin et al. . |
| 5,827,218 | 10/1998 | Nguyen et al. . |
| 5,899,884 | 5/1999 | Cover et al. . |

*Primary Examiner*—Wynn Wood Coggins
*Assistant Examiner*—Deborah Blyveis
*Attorney, Agent, or Firm*—Flynn, Thiel, Boutell & Tanis, P.C.

[57] ABSTRACT

A fluid management pump system (20) for applying an irrigation/distention solution to a surgical site. The system includes a pump (22) for forcing the solution through an inflow tube (28). A portable power pack (26) attached to the pup provides the energization current for actuating the pump. The solution is introduced into the surgical site from the inflow tube through a first cannula (30) across which there is a relatively small pressure drop. Fluid discharged from the surgical site is drained from the site through a second cannula (32) across which there is a low pressure drop. A hand controller (38) is attached to the inflow and outflow tubes. The hand controller contains a valve (46) for regulating fluid flow through the outflow tube. A pump control circuit (232) is also disposed in the hand controller. Based on the actuation of buttons (42, 44) mounted to the hand controller, the pump control circuit regulates the energization signal applied to the pump so as to regulate the rate at which solution is discharged from the pump.

1 Claim, 11 Drawing Sheets

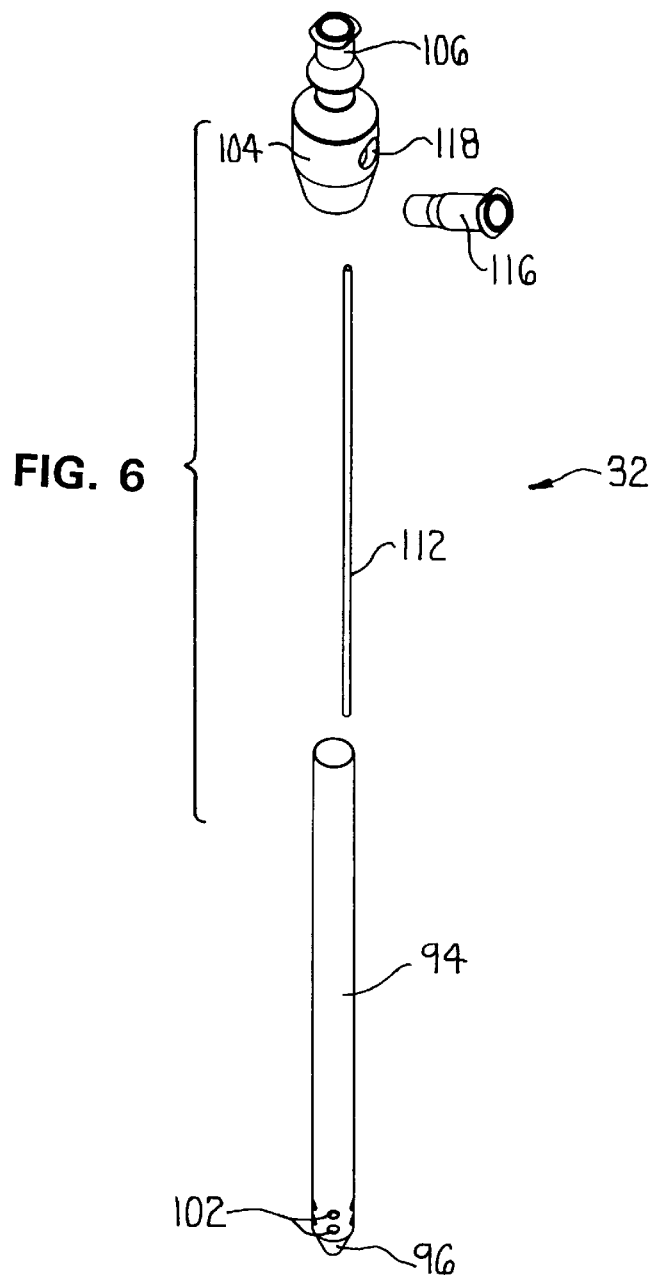
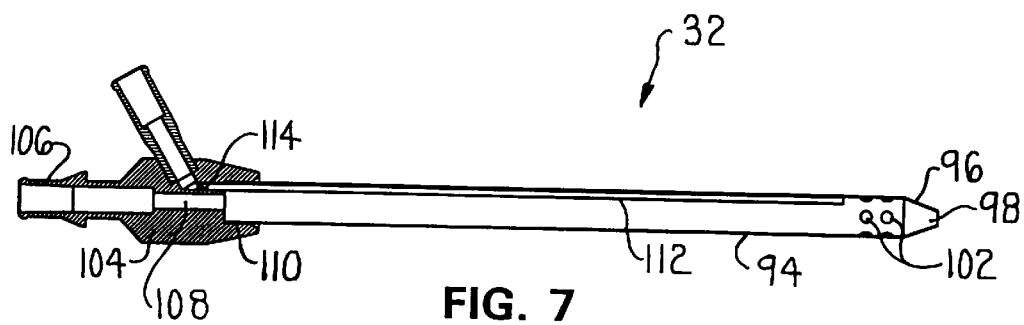

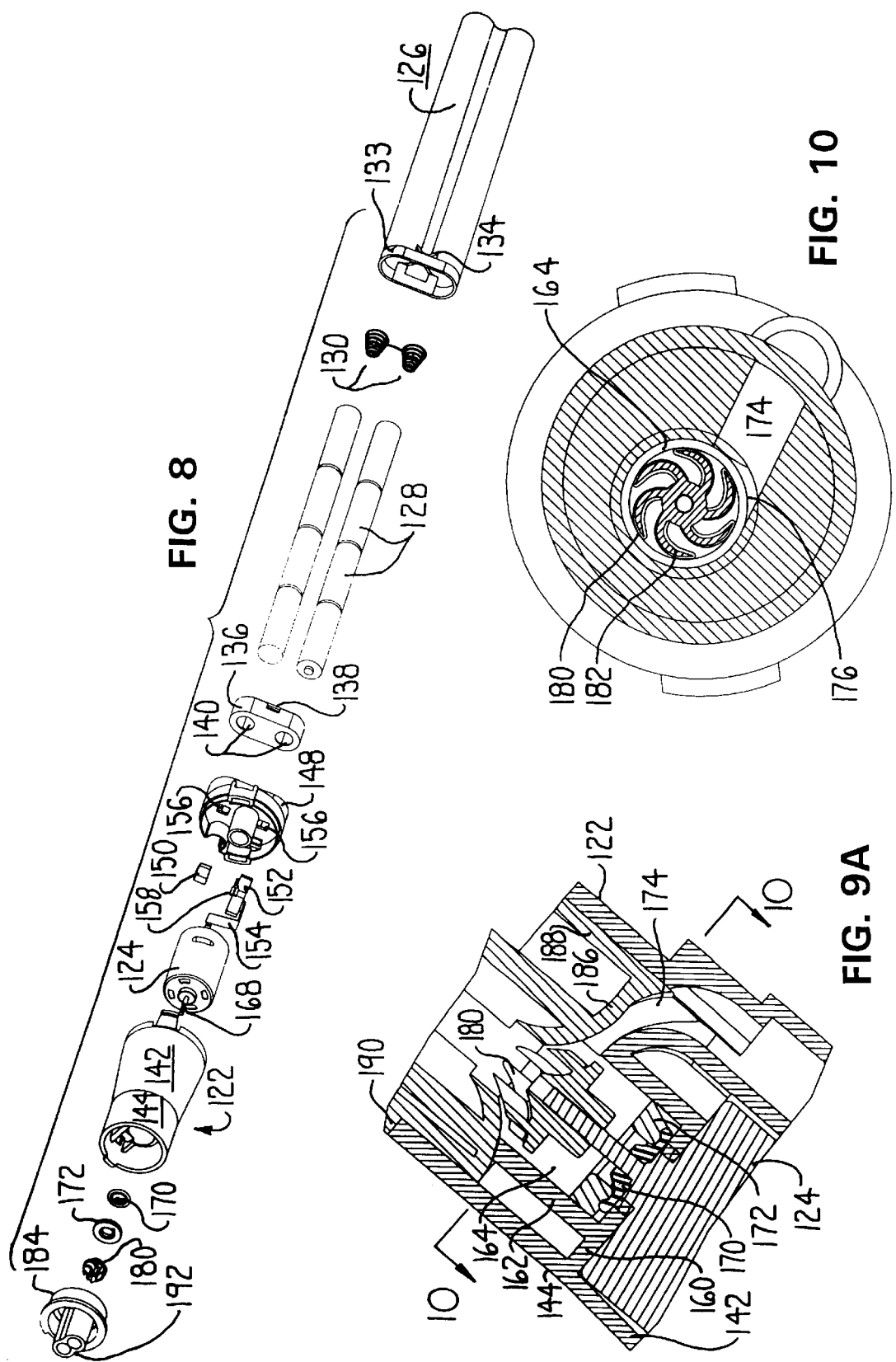

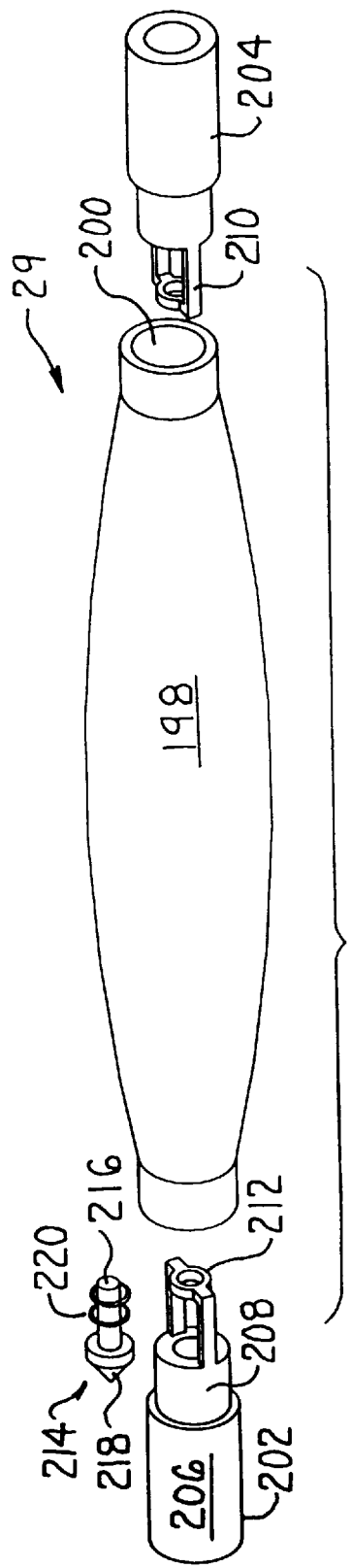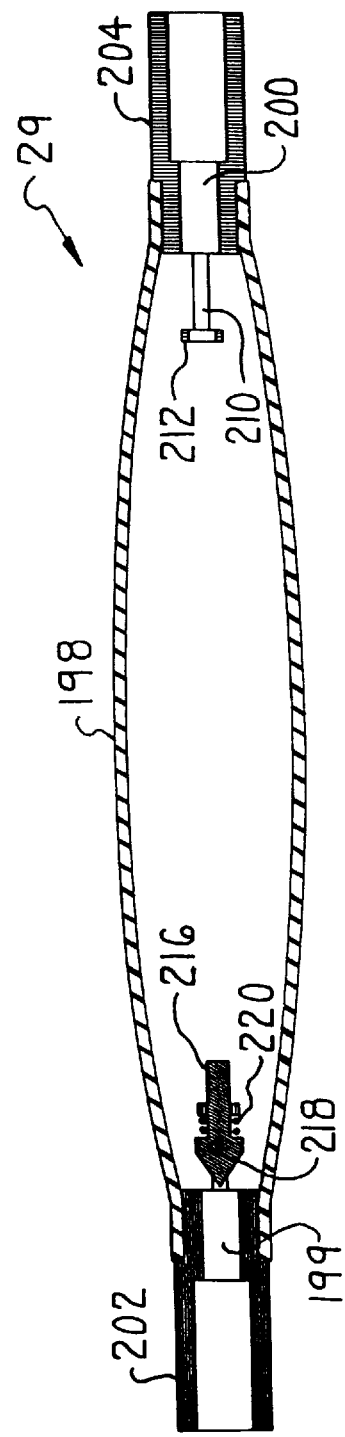
FIG. 11
FIG. 12

SELF-CONTAINED FLUID MANAGEMENT PUMP SYSTEM FOR SURGICAL PROCEDURES

FIELD OF THE INVENTION

This invention relates generally to fluid management pumps used for surgical procedures. More particularly, this invention relates to a self-contained fluid management pump system that does not require a supplemental power supply or controller.

BACKGROUND OF THE INVENTION

Fluid management pump systems are employed during surgical procedures to introduce sterile solution into surgical sites. For example, a fluid management pump may be employed during an endoscopic surgical procedure. In endoscopic surgery, an endoscope is inserted into the body through a small opening known as a portal. The endoscope is positioned at the site where the surgical procedure is to be performed. The endoscope is a surgical instrument that provides a view of the portion of the body in which it is inserted. Other surgical instruments are placed in the body through-other portals and are positioned at the surgical site. The surgeon views the surgical site through the endoscope in order to determine how to manipulate the other surgical instruments. The development of endoscopes and their companion surgical instruments has made it possible to perform minimally invasive surgery that eliminates the need to make large incisions to gain access to the surgical site. An advantage of performing endoscopic surgery is that, since the portions of the body that are cut open are minimized, the portions of the body that need to heal are likewise reduced. Still another advantage of endoscopic surgery is that it exposes less of the patient's internal tissues and organs to the open environment. This minimal opening of the patient's body lessens the extent to which these internal tissues and organs are exposed to infection.

The ability to perform endoscopic surgery is enhanced by the development of fluid management pumps. A fluid management pump pumps a sterile solution into the enclosed portion of the body at which the endoscopic surgical procedure is being performed. This pressure of this solution expands, distends, and separates the tissue at the surgical site so as to increase both the field of view of the site and the space available to the surgeon for manipulating the instruments. One type of endoscopic surgery in which fluid management pumps have proven especially useful is in arthroscopic surgery. In arthroscopic surgery, a specially designed endoscope, called an arthroscope, is employed to examine inter-bone joints and the ligaments and muscles that connect the bones. A fluid management pump is often employed in arthroscopic surgery to expand the space between the bones and adjacent soft tissue in order to increase the field in which the surgeon can perform the intended surgical procedure. Fluid management pumps are, during arthroscopic surgery, used to increase the surgical view and working space around the joints that form an elbow, a knee, a wrist or an ankle. During arthroscopic surgery, the pressure of the fluid introduced by the pump also reduces and contains the internal bleeding at the surgical site. Moreover, fluid management pumps are used in both endoscopic surgery and in other surgical procedures to remove debris generated by the procedure.

The Applicant's U.S. Pat. No. 5,810,770, entitled FLUID MANAGEMENT PUMP SYSTEM FOR SURGICAL PROCEDURES, issued Sep. 22, 1998, and incorporated herein by reference, discloses one conventional fluid management pump system. This particular system includes a pump that is used to force sterile solution to the surgical site. The pump is part of a tube set that includes a inflow line through which the fluid flows from the pump to the patient. The tube set also includes a second line, an outflow line, through which the fluid discharged from the surgical site is flowed to a collection container. The tube set has a third line for receiving a fluid column from the surgical site. The head of the fluid column in the third line is applied to a transducer which, in turn, generates a signal representative of the fluid pressure at the surgical site. This system also includes a control console to which the tube set is connected. In this particular system, the pressure transducer is located in the control console. The control console converts the line voltage into a signal suitable for energizing the pump. The control console also includes a pair of solenoids, each one of which is in close proximity with a separate one of the fluid inflow or outflow lines. Each solenoid regulates the open/closed state of a valve associated with a separate one of the inflow or outflow conduits.

The control console also includes a number of switches that allows the surgeon to regulate the fluid pressure and the rate of fluid flow through the surgical site. Based on the surgeon-set commands and the sensed fluid pressure at the surgical site, the control console selectively energizes the pump and opens and closes the inflow and outflow conduits.

While the above described fluid management pump systems work reasonably well, there are some disadvantages associated with their use. In particular, this type of system brings additional equipment, additional clutter, to the surgical suite. Moreover, many current fluid management systems are designed so that the control switches that are actuated to establish fluid flow rate and fluid pressure are mounted on the control console. This means that, when a surgeon wants to reset these settings, he/she must either personally be divert attention from the instruments and the surgical site in order to depress the buttons on the control console, or instruct an assistant to enter the new settings. There have been attempts to minimize this disruption by providing control consoles with separate hand controllers. This type of controller is connected to its associated console by a cable. While this type of remote controller works reasonably well, it brings another device and a complementary control line, both additional clutter, to the surgical suite. Moreover, as with any piece of reusable medical equipment, it is necessary to maintain these consoles and even sometimes necessary to repair them.

The cannulae with which many current fluid management pump systems are used also have their own shortcomings which detract from the utility of these systems. These cannulae are the rigid members that are inserted into the portals formed in the patient's body and that serve as the conduits through which the irrigating fluid is introduced into and drained from the surgical site. In practice, it is often necessary to provide three separate conduits to the associated tube set. A first conduit serves as the flow path through which fluid is introduced into the surgical site. A second conduit serves as the flow path through which fluid is discharged from the surgical site. Finally, there is a third conduit over which a column of fluid is withdrawn from the surgical site. This is fluid column that is applied to the complementary transducer in order to determine the fluid pressure at the surgical site. These cannulae, in addition to providing fluid conduits, also serve as the conduits through which instruments such as the endoscope/arthroscope are seated at the surgical site.

The problem associated with many of these cannulae is that the fluid flowing through them undergoes a significant pressure drop. For example, studies have shown that in a system designed to apply approximately 1.8 lit./min fluid flow, it is necessary to pump the fluid out of the pump at a pressure of approximately 18 psig in order to maintain the fluid at the surgical site at a constant pressure. Of this 18 psig of pressure, approximately 15 psig are lost in a pressure drop across one of the cannula. Thus, a significant amount of the power that is developed by the pump is expended in order to simply force the fluid through the cannulae. This means that large amounts of energy are applied to the pump solely to overcome this cannula-centered pressure drop. Consequently, it has been necessary to provide current control consoles with power converters that can deliver the large quantities of energy required by these pumps. The size of these power converters has contributed to making current control consoles, heavy, bulky pieces of equipment. Moreover, these power converters can significant amounts of waste heat.

Moreover, sometimes during a surgical procedure the outflow of fluid from the surgical site can be temporarily blocked. When this flow is so blocked, the pressure of the fluid output by the pump is not simply lost across the cannula. Instead, the pressure of this fluid will be up at the surgical site. If this pressure becomes too great, there is risk that the patient's tissue may become damaged.

SUMMARY OF THE INVENTION

This invention relates to an improved fluid management pump system. The fluid management pump system of this invention has a portable power pack so as to eliminate the need to provide a bulky supplemental control console. The controls used to regulate fluid flow and pressure are built into a hand controller that is mounted to the inflow and outflow tubes. The fluid management pump system of this invention also includes a cannula through which the fluid flowing through undergoes a minimal pressure drop as it is flowed to or discharged from the surgical site.

BRIEF DESCRIPTION OF THE DRAWINGS

This invention is pointed out with particularity in the claims. The above and further features of the invention may be better understood by reference to the following description taken in conjunction with the accompanying drawings in which:

FIG. 6 is an exploded view of the second low-loss cannula of this invention;

FIG. 7 is a cross sectional view of the cannula of FIG. 6;

FIG. 8 is an exploded view of the components forming the pump and power pack;

FIG. 9A is an enlarged cross sectional of the upper end of the pump depicting the conduit through which fluid is discharged from the pump;

FIG. 10 is a cross sectional view of a horizontal slice through the pump taken along line 10—10 of FIG. 9A;

FIG. 11 is an exploded view of the accumulator of this invention;

FIG. 12 is a cross sectional view of the accumulator;

DETAILED DESCRIPTION

Figure 1:
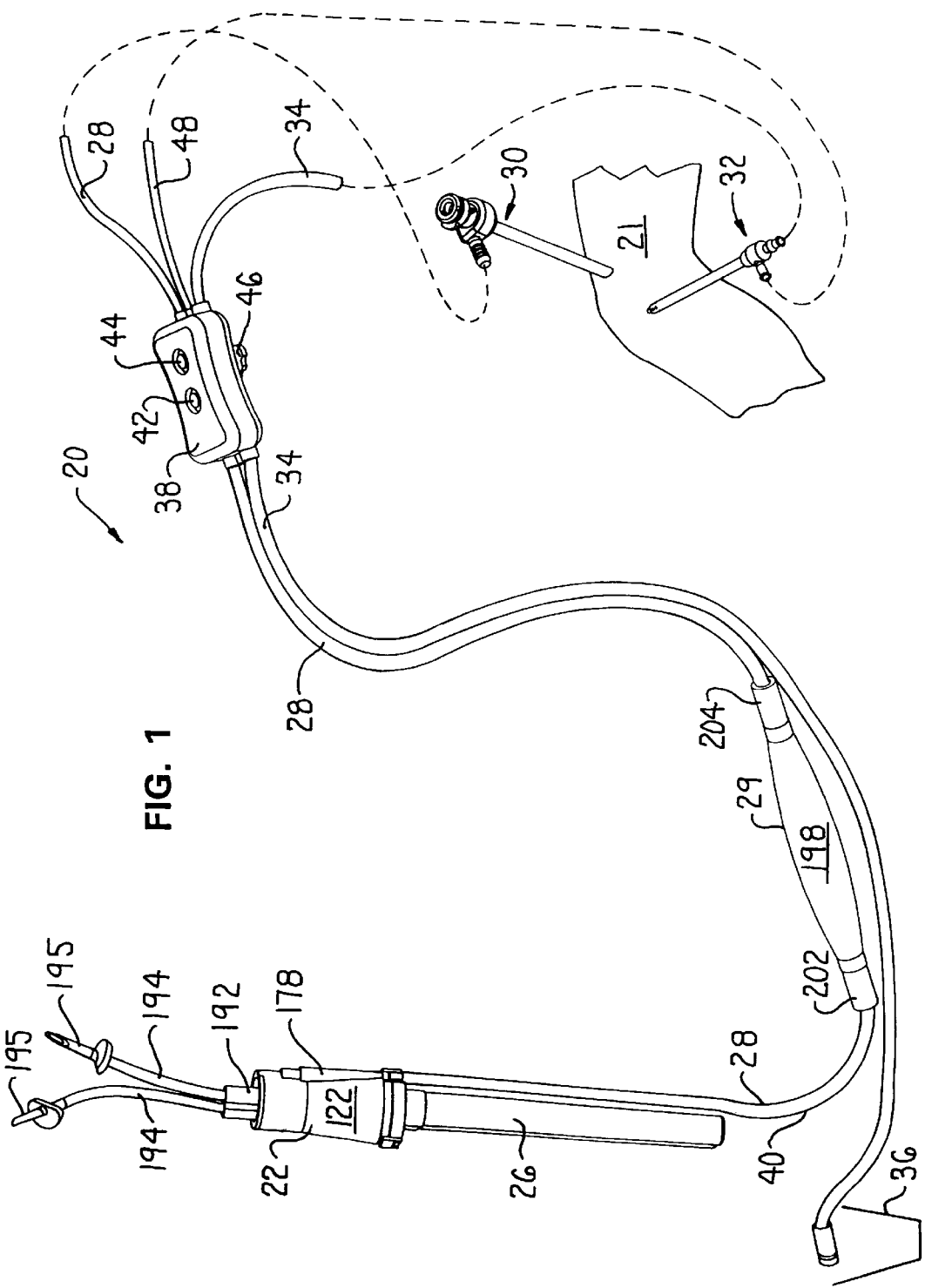
FIG. 1 depicts the basic components of the fluid management pump system of this invention.

FIG. 1 depicts a fluid management system 20 of this invention that is employed to supply a sterile distention solution to a surgical site within a body and, more particularly, the joint capsule of a knee 21. The system 20 includes a pump 22 which receives solution from supply bags (not identified). The pump 22 is electrically driven and is energized from a portable power pack 26 that is attached to and extends below the pump. The pump 22 forces the solution downline towards the surgical site through a flexible inflow tube 28. Initially, the fluid flows through an accumulator 29 that is in-line with the in flow tube 28. The fluid is applied from inflow tube 28 to the surgical site through a first low-loss cannula 30. Cannula 30, in addition to defining a conduit through which the fluid flows to the surgical site, defines a conduit in which an arthroscope, (not illustrated) is seated so that the arthroscope can be positioned at the surgical site. The fluid is discharged from the surgical site through a second low-loss cannula 32. An outflow tube 34 is connected to the proximal end of cannula 32 for receiving the discharged fluid. (Throughout this application "proximal" and "rearward" shall be understood to me away from the surgical site. "Distal" and "forward" shall be understood to mean towards the surgical site.) The discharged fluid flows through the outflow tube 34 to an appropriate collection container 36. The inflow tube 28 and the outflow tube 34 are connected together starting at a point forward of the accumulator 29.

A hand controller 38 is fitted over distal parallel sections of the inflow and outflow tubes 28 and 34, respectively. A cable 40 extends from the pump 22 and power pack 26 to the hand controller 38. In the depicted version of the invention, cable 40 is attached to the portion of inflow tube 28 that extends from pump 22. Hand controller 38 contains a circuit described hereinafter for regulating the energization signal applied to the pump 22. Two buttons 42 and 44 allow the surgeon to regulate the energization signal applied to the pump 22. The hand controller 38 also includes a flow control valve 46 for regulating fluid flow through outflow tube 34. By selective setting of energization signal applied to the pump 22 and the setting of the flow through outflow tube 34, the surgeon can control system 20 of this invention to regulate both the rate of fluid flow through the system and the fluid pressure at the surgical site.

In the depicted version of the invention, a flexible pressure measurement tube 48 extends from cannula 32 to the hand controller 38. A fluid column from the surgical site is applied to the hand controller 38 through tube 48. A transducer, described hereinafter, internal to the hand controller 38 measures the pressure of the fluid column to determine the fluid pressure at the surgical site. The circuit internal to the hand controller 38, based on a signal from the transducer, further regulates the actuation of the pump 22. In still more preferred versions of the invention, transducers internal to the hand controller 38 also monitor the flow rate of the fluid through the inlet and outlet tubes 28 and 34, respectively. The hand controller circuit also uses this flow rate data to further regulate the energization of pump 22.

Figure 2:
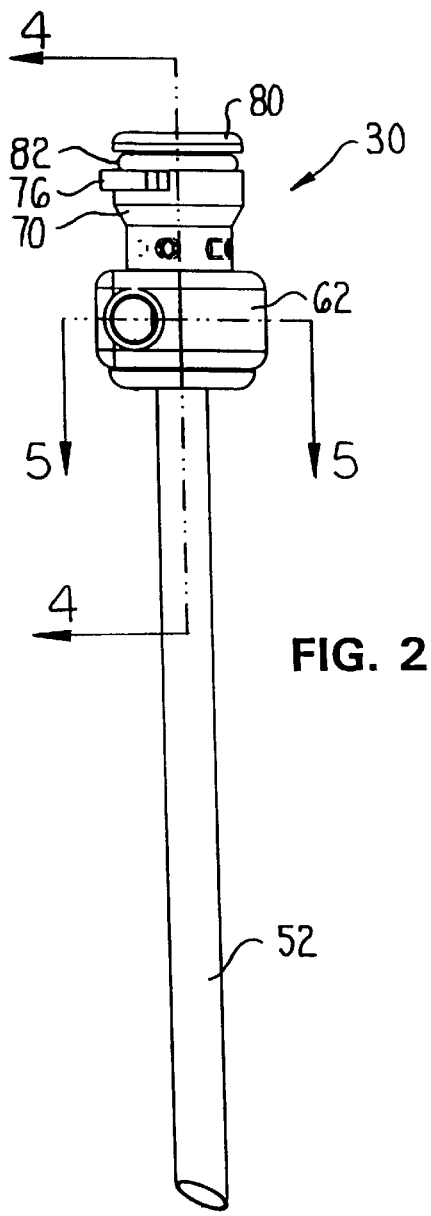
FIG. 2 is a side view of the first low-loss cannula of this invention.
Figure 4:
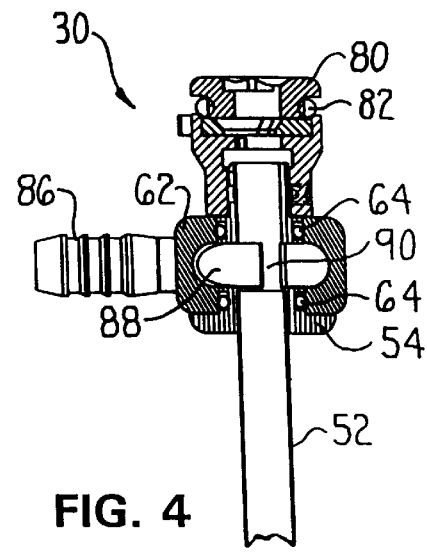
FIG. 4 is a cross-sectional view of the proximal end of the cannula of FIG. 2.
Figure 3:
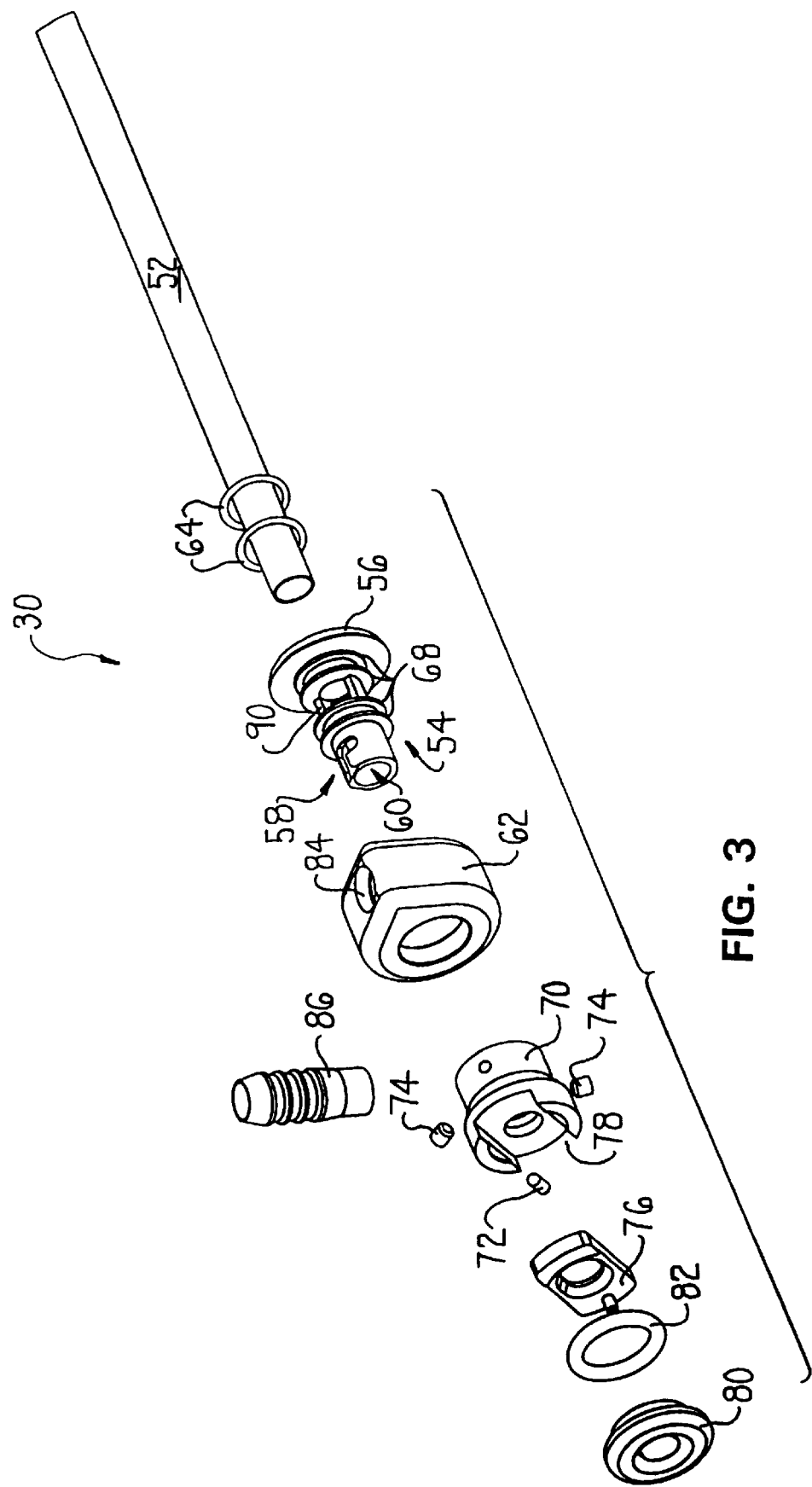
FIG. 3 is an exploded view of the cannula of FIG. 2.

The first low-loss cannula 30 is now described by initial reference to FIGS. 2–4. Cannula 30 includes an elongated sleeve-like shaft 52. The proximal end of shaft 52 is seated in the distal end of a hub 54. The hub 54 has a disk-like base 56 which functions as the distal bottom end of the hub. A skeletal frame 58 extends rearward from base 56. Frame 58 has a generally circular cross sectional profile. Collectively, base 56 and frame 58 are shaped to define a bore 60 that extends axially through the hub 54. Shaft 52 is permanently mounted in the distal end of bore 60. A body 62 extends over frame 58 and rests against the rearward facing surface of base 56. Body 62, as described hereinafter, is the component of the cannula 30 through which fluid transits. Two O-rings 64 that extend around frame 58 provide a liquid tight seal between the frame and the body 62. A first one of the O-rings 64 is located immediately above the forward-facing surface of hub base 56. A second one of the O-rings 64 extends around the proximal end of a bore 66 that extends axially through body 62. Annular flanges 68 that are part of hub frame 58 hold O-rings 64 in position.

A lock base 70 is fitted over the proximal end of hub frame 58 that extends rearward of body 62. A pin 72 extends through the lock base 70 and seats in a small bore in the hub frame 58 to ensure that the lock base is properly positioned relative to the hub 54, (frame bore not identified). Set screws 74 secure the lock base 70 to the hub frame 58. A lock tab 76 is slidably mounted in a notch 78 formed in the forward end of the lock base 70. A circular scope piece 80 is secured to the lock base 70 over the lock tab 76. A lock O-ring 82 is fitted around the scope piece 80. Collectively, lock base 70, lock tab 76, scope piece 80 and lock O-ring 82 form an assembly for releasably holding an endoscope/arthroscope to cannula 30. A more complete discussion of how this assembly functions is found in the Assignee's U.S. Pat. No. 5,456,673, entitled, LOCKING CANNULA FOR ENDOSCOPIC SURGERY, issued Oct. 10, 1995, which is incorporated herein by reference.

Figure 5:
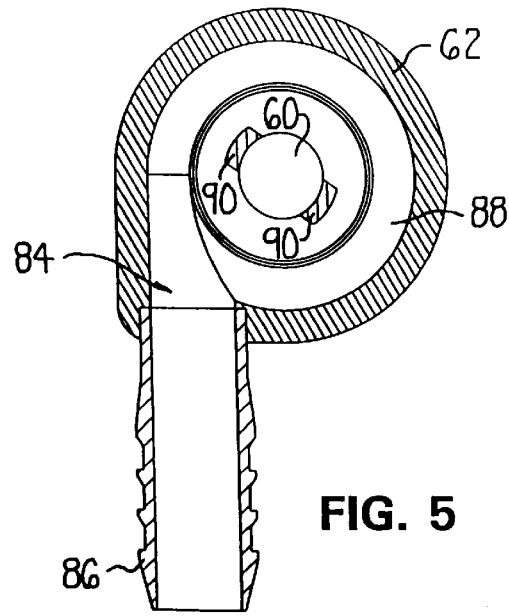
FIG. 5 is a cross sectional view of a horizontal slice of the cannula of FIG. 2 taken along line 5—5 of FIG. 2.

The structure of body 62 of cannula 30 is now described in greater detail by reference to FIGS. 3–5. Body 62 is formed so as to have an opening 84 in which a hose barb 86 is seated. The hose barb 86 is a short tubular member to which the associated fluid tube, here inflow tube 28, is attached. Cannula body 62 is formed so that opening 84 is offset from the longitudinal axis that extends through shaft 52 and hub bore 60. More particularly, the body 62 is formed so that the cross sectional space subtended by opening 84 does not subtend the cross sectional space subtended by hub bore 60. Cannula body 62 is further formed so as to have a center space 88 with a circular cross sectional profile that completely surrounds and is in fluid communication with hub bore 60. Center space 88 is the space internal to the body 60 with which opening 84 is in direct fluid communication. Cannula body 62 is further formed so that inner wall thereof that defines the outer perimeter of center space 88 has is curved. The cannula body 62 is shaped so that center space 88 has a diameter equal to the sum of the diameter of the hub bore 60 and the diameter across opening 84. Thus, the cross-sectional flow path through opening 84 and in center space 88 around hub bore 60 are essentially identical.

The hub frame 58 is formed so as to have two diametrically opposed, spaced apart legs 90 that extend through body center space 88. Each leg 90 extends from the flange 68 that is immediate rearward relative to distal O-ring 64 to the flange 68 that is immediately forward of proximal O-ring 64. When fluid is flowing through cannula 30, it flows between body center space 88 and hub bore 60/shaft 52 through the gaps between legs 90.

FIGS. 6 and 7 illustrate the structure of the second low-loss cannula 32 of this invention. Cannula 32 includes an elongated hollow shaft 94. Shaft 94 is formed to have a distal end with an inwardly directed taper 96. The shaft 94 is further formed to have a single opening 98 at the distal end thereof. Owing to taper 96, opening 98 has a diameter less than the diameter of the inside wall of shaft 94. A number of auxiliary openings 102 are formed in the distal end of shaft 94 immediately rearward of tapered section 96. Openings 98 and 102 collectively form a colander that allow significant fluid flow from the surgical site into shaft 94 while preventing medium sized debris from becoming entrained in this fluid flow.

A head 104 is fitted over the proximal end of shaft 94, the end of the shaft located above the portal in which the shaft is seated. Head 104 is formed so as to have a proximal end that is shaped to function as a hose barb 106 to which the outflow tube 34 is connected. A through bore 108 extends axially through head 104 from hose barb 106 to the distal end of the head. The proximal end of shaft 94 is seated in a counterbore 110 integral with bore 108 in the distal end of the head 104.

Cannula 32 also includes a sample tube 112 that is welded or otherwise permanently secured to the inside wall of shaft 94. Sample tube 112 is of relatively small diameter. For example, if shaft 94 has an inner diameter of approximately 0.200 inches, sample tube 112 has an outside diameter of approximately 0.040 inches. The distal end of sample tube 112 is located immediately rearward of openings 102 in shaft 94. The proximal end of sample tube 112 extends rearward out of shaft 94. The portion of the sample tube 112 that extends rearward of shaft 94 is seated in an auxiliary bore 114 formed in head 104 that is parallel with and spaced from through bore 108. More specifically, auxiliary bore 114 extends rearward from a stepped surface between through bore 108 and counterbore 110. Head 104 is provided with a sensing barb 116 that is in fluid communication with sample tube 112 through auxiliary bore 114. Sensing barb 116 is a hose barb designed to receive pressure measurement tube 48. The sensing barb 116 is fitted in a hole 118 formed in the side of head 104 that is in fluid communication with auxiliary bore 114. More particularly, head 104 is formed so that hole 118 meets auxiliary bore 114 at an angle of approximately 45°.

The pump 22 and power pack 26 are now initially described by reference to FIGS. 1 and 8. Pump 22 includes a chassis 122 that contains the motor 124 and other moving components of the pump. Power pack 26 includes a shell 126 in which the energy-providing batteries 128 for the system 20 of this invention are housed. In the depicted version of the invention, shell 126 is shaped to hold two rows four series-connected batteries 126. Two conically shaped coil springs 130 are seated in the base of shell 126. Springs 130 urge the rows of batteries towards chassis 122 so that the lead battery of each row physically abuts an associated contact mounted in the chassis. The springs 130 are connected together so as to establish a series connection between the rows of batteries 126. Integrally formed with shell 126 is a flat, oval-shaped reinforcing ring 133 that extends around the open end of the shell. A flexible tab 134 extends downwardly and outwardly from the opposed straight sections of reinforcing ring 133. A shell cap 136 is fitted over the open end of shell 126 and the batteries 126 contained therein. Shell cap 136 is formed with a base that has opposed openings 138. Tabs 134 extend through openings 138 so as to hold cap 136 to the shell 126. Shell cap 136 is form with a top that has two through holes 140. Holes 140 serve as access ports through which the contacts extend so that the contacts can abut batteries 128.

Figure 9:
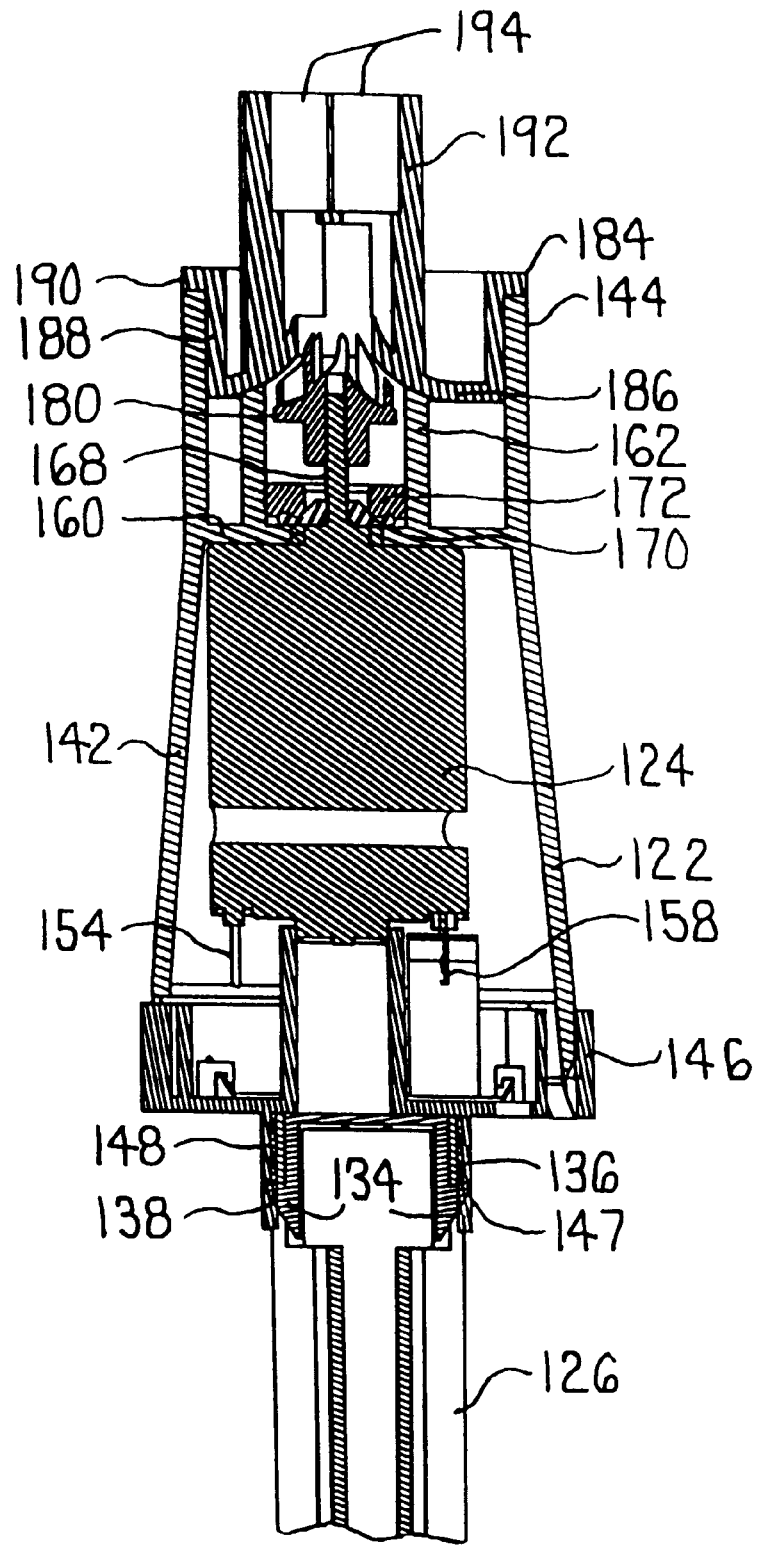
FIG. 9 is a cross sectional view of the moving components of the pump.

Pump chassis 122 (described by reference to FIGS. 9, 9A and 10) has a lower frusto-conical section 142 in which the motor 124 is seated. Integrally formed with and located above frusto-conical section 142, chassis 122 is shaped to have a constant diameter section 144. The irrigation/distention solution is gravity flowed into the constant diameter section 144 of the chassis and forced out of the section by the pumping action. A bottom cap 146 is snap fitted to the open bottom end of the chassis frusto-conical section 142. The bottom cap is formed with a downwardly directed, oval shaped, open ended sleeve 148. Sleeve 148 is shaped to receive shell cap 136 and the upper end of shell 126. The inner surface of sleeve 148 is formed with two opposed notches (147). The outer ends of shell tabs 134 extend through cap holes 140 and seat in the sleeve notches so as to hold the power pack 26 to the chassis 122. The exposed ends of tabs 134 can be depressed inwardly so that the tabs retract away from the notches. The separation of the tabs 134 from the back cap sleeve 148 allows the power pack 26 to be separated from the pump 22. Bottom cap 146 is formed to have a center-located, upwardly extending, tube-shaped mounting post 149. Motor 124 is seated on mounting post 149.

Three flat contacts 150, 152 and 154 are seated in bottom cap 146. Contacts 150 and 152 are seated in openings 156 formed in the base of the bottom cap 146 and are the contacts that physically abut the batteries 128. The third contact 154 extends from the positive terminal of the motor 124 (terminal not illustrated) to contact 150, the contact associated with the positive terminal of the batteries 128. Also depicted in FIG. 8 is a conductive connector 158. Connector 158 provides a conducive path between the negative terminal of the motor 124 and a wire that extends to hand controller 38 (motor terminal and wire not illustrated).

Pump chassis 122 is formed to have a flat, ring shaped lip 160 that extends inwardly from the inner wall of the chassis along the plane at which the constant diameter section 144 extends from frusto-conical section 142. Chassis 122 is further formed to have a tubular web 162 that extends upwardly from the inner surface of lip 160. The space above lip 160 within web 162 functions as the pump chamber 164 for the pump 22.

When the pump 22 is assembled, the top surface of the motor 124 presses against the rearwardly directed face of lip 160. Motor 124 has a rotating shaft 168. Shaft 168 extends through the circular opening defined by the inner perimeter of lip 160 into pump chamber 164. The shaft 168 extends through a lip seal 170 located in the base of the pump chamber 164 and that rests against the inner portions of lip 160. The ring-shaped hoop 172 formed of plastic extends around the shaft 168 and is pressed against the outer portion of the forward-directed face of lip seal 170. Hoop 172 is compression fitted against web 162 and holds lip seal 170 in position.

As best seen by FIGS. 9A and 10, pump chassis 122 is further formed to have an outlet conduit 174 that expends from pump chamber 164. The chassis 122 is shaped so that conduit 174 extends from an opening 176 in web 162 along an axis that is offset from the axis of motor shaft 168. The plastic forming conduit 174 is shaped so that, downstream from opening 176, the conduit curves downwardly so that the distal end thereof is parallel to the axis of the motor shaft 168. In order to form the conduit 174 it will be noted that the outside of the chassis 122 has a raised rib 178 that extends from approximately the mid-level of the chassis constant diameter section 144 downwardly along the complete length of the frusto-conical section 142. Chassis is further formed so that the downstream section of conduit 174 that runs parallel to the motor shaft 168 has a diameter that is greater than the diameter of the portion of the conduit adjacent the pump chamber 164. The increased diameter of this section of the conduit 174 facilitates the seating of the proximal end of the inflow tube 28 in this portion of the conduit.

While not show, it should be understood that the pump chassis 122 is further formed with a small opening that opens into conduit 174 adjacent the distal bottom open end of the conduit. This opening is the opening through which cable 40 extends. Downline from this opening, cable 40 is secured by an adhesive or other suitable means to the outer surface of inflow tube 28.

An impeller 180 is mounted over the free end of motor shaft 168 in pump chamber 164. The impeller 180 is shaped to have vanes 182 that are forward swept. That is, vanes 182 have a curved profile such that as they extend outwardly from the center of the impeller, they curve in the direction of rotation of the impeller 180. It will be observed that the impeller 180 is spaced inwardly from the adjacent chassis web 162 and is spaced above the top of hoop 172. This arrangement serves to minimize the friction that develops when the pump 20 is actuated.

A circular top cap 184 is compression fitted over the top of the pump chassis 122 and the pump chamber 164. Top cap 184 has a base 186 that is seated in the open end of chassis constant diameter section 144. An annular side wall 188 extends upwardly from base 186 and presses against the inner surface of the chassis constant diameter section 144. An outwardly directed flange 190 extends perpendicularly away from the top of side wall 188. Flange 190 limits the downward movement of top cap 184 towards chassis 122. An inlet sleeve 192 expends upwardly from base 186 above side wall 188. The sleeve barb 192 is centered over center axis of the impeller 180. Inlet sleeve 192 is formed with two openings so that supply lines 194 (FIG. 1) from two supply bags can be connected to the pump 22. Inlet spikes 195 are fitted to the ends of supply lines 194 for connecting the proximal ends of the lines to the supply bags.

The structure of the accumulator 29 is now described by reference to FIGS. 1, 11 and 12. The body of the accumulator is an elastic, elongated tubular balloon 198. The balloon 198 is shaped to have an inlet opening 199 at one end through which solution flows into the balloon and an outlet opening 200 at the opposed end through which solution flows from the balloon. Balloon 198 is formed of an elastomer such as low-durometer silicon rubber, so that the balloon can both expand and, when the solution therein can flow, contract.

Inflow and outflow connectors 202 and 204, respectively, are seated in the opposed open ends of the balloon 198. Connectors 202 and 204 are identical in shape. Each connector 202 and 204 has a tubular body 206 in which end sections of inflow tube 28 are seated. A tube-like sleeve 208 extends from each body 206. Sleeves 208 have both inner and outer diameters that are less than the diameters of the associated bodies 206. Sleeve 208 of inflow connector 202 is seated in the inlet opening 199. Inflow connector 202 thus serves as the component that connects the portion of inflow tube 28 that extends from the pump 22 to the accumulator 29. Sleeve 208 of outflow connector 204 is seated in outlet opening 200. Outflow connector 204 thus serves as the component that connects the portion of the inflow tube 28 that extends downline from the accumulator 29 to the hand controller 38.

A pair of diametrically opposed fingers 210 extend from each connector sleeve 208. A circular web 212 is attached to the end of each opposed pair of fingers 210 and held in place by the fingers. The opening defined by each web 212 is coaxial with the bores that extend through the associated connector body 206 and sleeve 208, (openings and bores not identified). A plunger 214 is mounted to inflow connector 202. Plunger 214 has a stem 216 that extends through the opening in the associated connector web 212. Integral with the stem 216, the plunger 214 has a conical shaped head 218 that is directed towards the open end of inflow connector sleeve 208. A spring 220 is fitted around stem 216. Spring 220 extends between web 212 and the opposed surface of the plunger head 218 so as to bias the plunger towards sleeve 208. Spring 220 has a biasing force that holds the plunger 218 against the inlet connector sleeve 208 when there is no fluid flow from the pump 22 and that allows the head to retract away from the sleeve when there is anything more than a nominal fluid flow from the pump.

Figure 13:
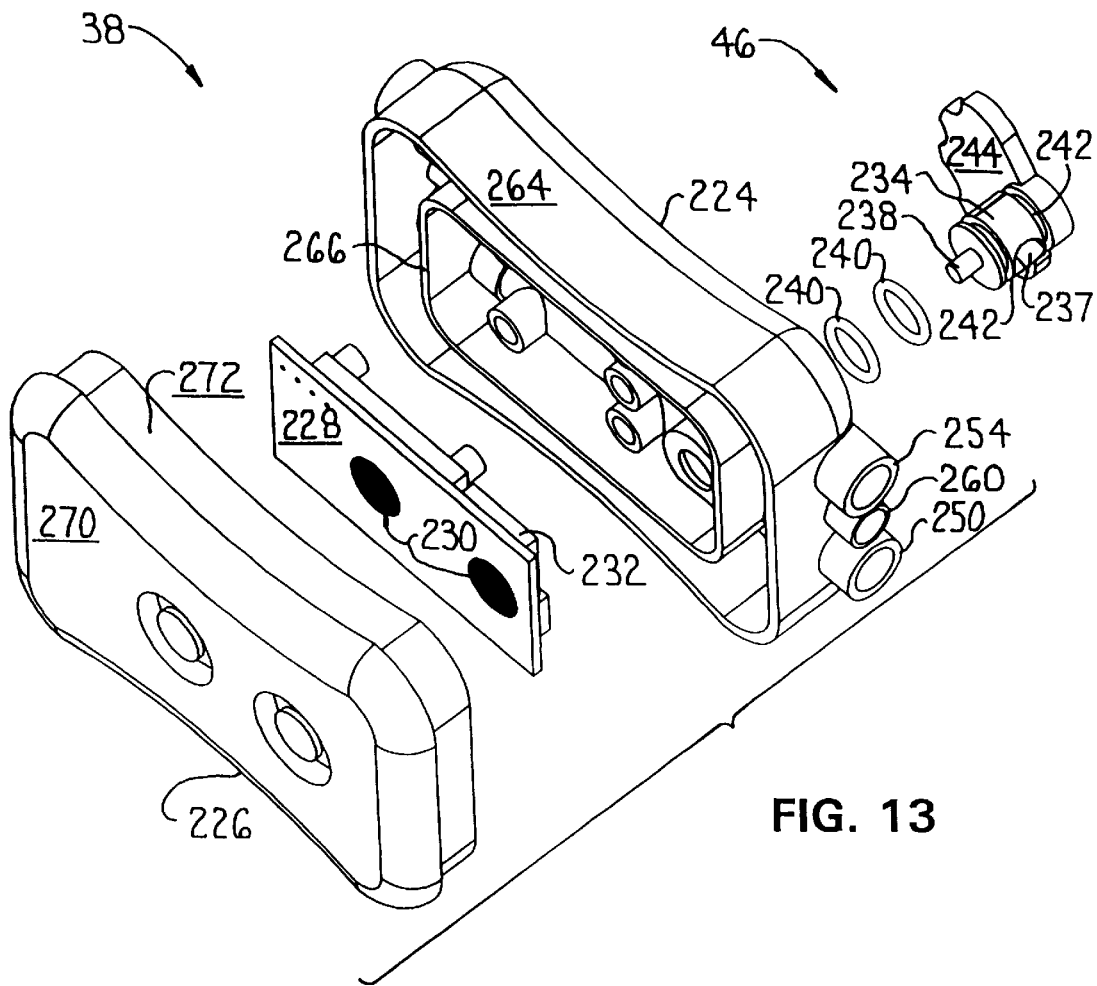
FIG. 13 is an exploded view of the hand controller of this invention.

The hand controller 38, as seen by FIG. 13, includes a chassis 224 that serves as the base of the controller and a key pad 226 that extends over the open top of the chassis. A printed wiring board 228 is mounted inside key pad 226. Printed wiring board 228 contains the transducers that monitor fluid flow through the hand controller 38 and the pressure of the fluid at the surgical site. Manually-actuated, momentarily-on switches 230 are mounted to the printed wiring board 228 to allow the surgeon to regulate operation of the fluid management pump system 20 of this invention. For example, in some versions of the invention switches 230 are membrane-type switches. Also mounted to the printed wiring board is a control circuit 232 that receives signals from transducers and switches 230. Based on these inputs, control circuit 232 regulates the actuation of pump 22 by regulating the application of energization signals to the pump. In some versions of the invention, control circuit 232 may be a single one of or pair of application specific integrated circuits (ASICs).

The flow control valve 46 is mounted to hand controller chassis 224. The valve 46 has a body 234 that is seated in bore 236 formed in chassis 224. The body 234 has a through hole 237 through which fluid can selectively flow. Seals 240, in the form of O-rings, are seated in annular grooves 242 formed in the opposed ends of valve body 234. The seals 240 provide a liquid tight barrier around the valve body 234.

Figure 16:
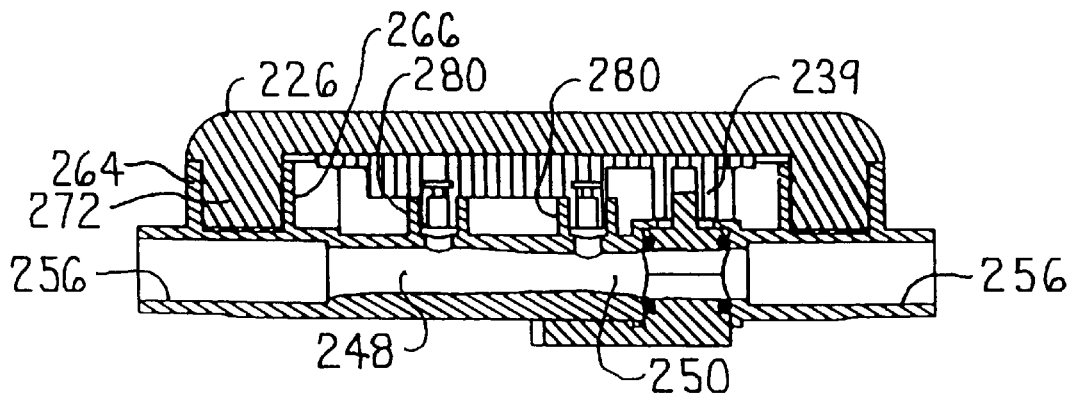
FIG. 16 is a cross sectional view of the hand controller depicting the flow path of fluid discharged from the surgical site through the controller.
Figure 17:
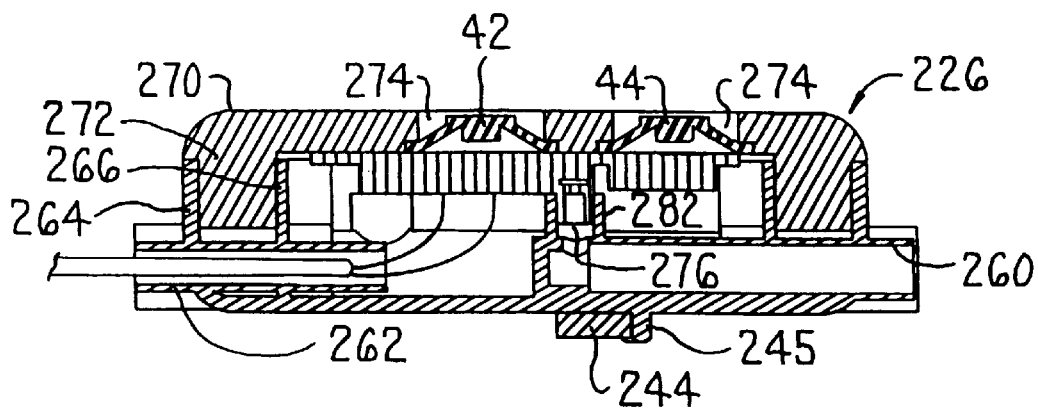
FIG. 17 is a cross sectional view depicting how the variable-pressure water column from the surgical site is applied to the hand controller.

A small post 238 extends downwardly from the base of valve body 234. The post 238 is snap fitted for rotation in a complementary open ended mounting boss 239 (FIG. 16) mounted to the printed wiring board 228. Flow control valve 46 also has a control lever 244 that is integrally formed with the valve body 234. A surgeon sets the rotational position of the valve body 234 by moving the control lever 244 in order to regulate the flow of fluid from the surgical site. A rib 245, shown in cross section in FIG. 17, is integrally formed on the exposed face of chassis 224 adjacent the control lever 244. Rib 245 limits the movement of the control lever 244 to cause a like limitation of the rotation of valve body 234.

Figure 14:
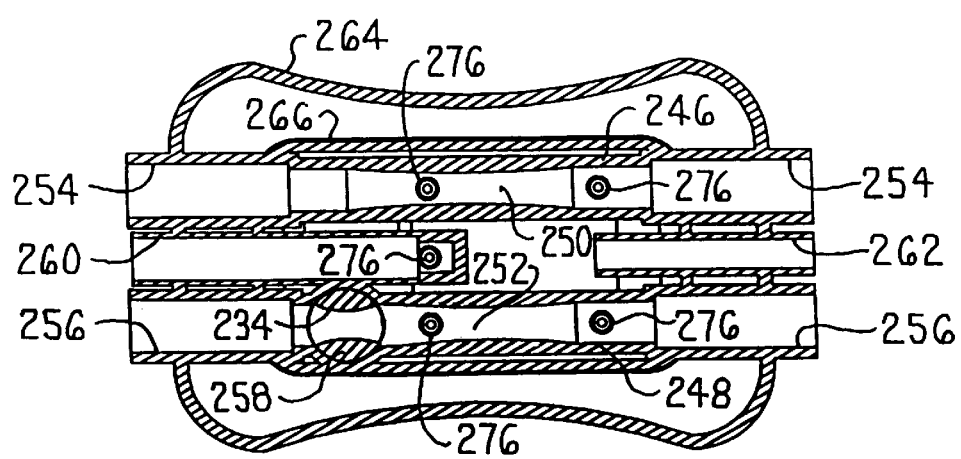
FIG. 14 is a cross sectional view of the chassis of the hand controller depicting the fluid paths through the hand controller.

The handpiece chassis 224, now described by reference to FIGS. 13 and 14, is shaped to have two rigid internal tubes 246 and 248 that extend through the chassis. Tube 246 functions as the conduit through which irrigation/distention solution flows through the hand controller 38 to the surgical site. Tube 248 functions as the conduit through which the fluid discharged from the surgical site drains through the hand controller 38 to container 36.

Tubes 246 and 248 are formed so that the opposed ends thereof have the approximately same constant diameter inner wall. Tubes 246 and 248 are further formed so that their center sections 250 and 252, respectively, have a venturi profile. Thus, the middle of each tube center section 250 and 252 is the smallest diameter portion of the conduit through the tube. The purpose of this construction will be obtained hereinafter. Tube 246 is further formed to have receiving sleeves 254 that are located at the opposed ends of the tube. Tube 248 is further formed to have receiving sleeves 256 that are located at the opposed ends of the tube. Each receiving sleeve 254 and 256 extends a short distance outside of the adjacent end of the handpiece chassis 224. Receiving sleeves 254 and 256 have inner diameters that are dimensioned slightly large than that of the adjacent inside diameters of the associated tubes 246 and 248, respectively. The ends of the sections of the inflow tube 28 that are coupled to controller tube 246 are fitted in receiving sleeves 254. The end of the sections of the outflow tube 34 that are coupled to controller tube 248 are fitted in receiving sleeves 256.

Controller tube 248, is further formed so as to have a receiving space 258 which is located in the controller 38 so as to be distal relative to the venturi-profiled center section 252. Receiving space 258 is shaped to accept the body 234 of flow control valve 46. Thus, by setting the rotational position of valve body 234 in the receiving space 258, valve body through hole 237 is selectively moved in and out registration with the center of tube 248. This action regulates the fluid flow through hand controller 38 and from the surgical site.

Handpiece chassis 224 is further formed to have a rigid measurement conduit 260. In the depicted version of the invention, measurement conduit 260 extends out of the end of the chassis directed towards the patient and is located between controller tubes 246 and 248. The measurement conduit 260 is formed so that the end of the conduit located inside chassis 224 is closed. The proximal end of pressure measurement tube 48 is fitted in the open end of measurement conduit 260.

The handpiece chassis 224 is further formed with an tube-shaped electrical conduit 262. In FIG. 14, conduit 262 is depicted as being axially aligned with measurement conduit 260 and shown extending out of the proximal end of the chassis. Conduit 262 is the member through which cable 40 extends into the hand controller 38. Not identified are the wires within cable 40 that are connected to the control circuit 232 through contacts on printed wiring board 228.

Handpiece chassis 224 is further formed so as have an outer wall 264 that serves as the outer side wall of the handpiece controller 38. Chassis 224 also has an inner wall 266 that is spaced inwardly from outer wall 264 and that, like inner wall 264, extends upwardly from the base of the chassis. The outer and inner walls 264 and 266, respectively, are the portion of the chassis through which receiving sleeves 254 and 256, measurement conduit 260 and electrical conduit 262 extend.

Controller key pad 226 has a flat base 270. A solid lip 272 extends perpendicularly around base 270 and is spaced inwardly a slight distance from the outer perimeter of the base. When the hand controller 38 is assembled, key pad lip 272 is seated in the interstitial space between outer and inner walls 264 and 266, respectively, of chassis 224.

The inner surface of key pad base 270 is the surface to which the printed wiring board 228 is mounted. Mounted in separate holes 274 forming in the base 270 are buttons 42 and 44. Each button 42 and 44, when depressed, closes a separate one of the membrane switches 230 mounted on the adjacent outer surface of printed wiring board 228.

Figure 15:
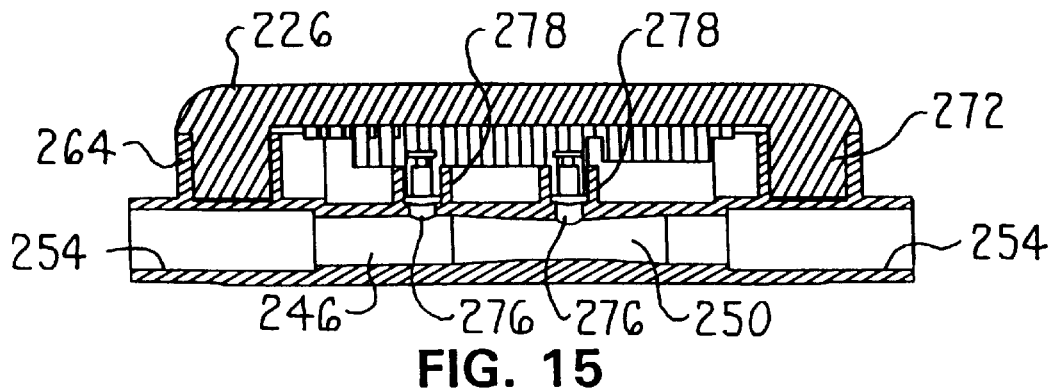
FIG. 15 is a cross sectional of the hand controller depicting the flow path of the irrigation/distention solution through the controller to the surgical site.

Five transducers 276 are mounted to the printed wiring board 228 for monitoring the pressure of the fluids flowing through and to hand controller 38. Each transducer 276 extends downwardly from the printed wiring board towards the chassis 224. As seen in FIG. 15, chassis tube 246 has two ports 278 through which two of the transducers 276 extend into the center of tube 246. Specifically, one of the transducers 276 extends into the distal constant diameter section of tube 246. The second transducer 276 extends into the smallest diameter portion of the tube center section 250. Similarly, as shown in FIG. 16, chassis tube 248 has two ports 280 through which two of the other transducers 276 extend. In tube 248 a first one of the transducers 276 is located in the smallest diameter portion of the tube center section 252. The remaining transducer 276 is located in the constant diameter section of tube 248 that is located downstream and proximal from center section 252.

The transducers 276 in chassis tubes 246 and 248 are employed to provide an inferential measurement of flow through the tubes. Specifically, for versions of the invention employing these transducer 276, the following information is thus known for each tube: the ratio of the area of the tube flow paths between the wide and narrow sections of the tube; and the ratio of the pressure of the fluid flow between the wide and narrow sections of the tube. Based on this data, the rate of fluid flow through each tube 246 and 248 can be calculated.

As depicted in FIG. 17, the fifth transducer 276 is mounted in a port 282 formed in measurement conduit 260. This transducer 276 is located adjacent the closed end of conduit 260. The fifth transducer 276 measures the fluid pressure of the fluid column that is applied to the hand controller 38 from the surgical site through pressure measurement tube 48.

Figure 18:
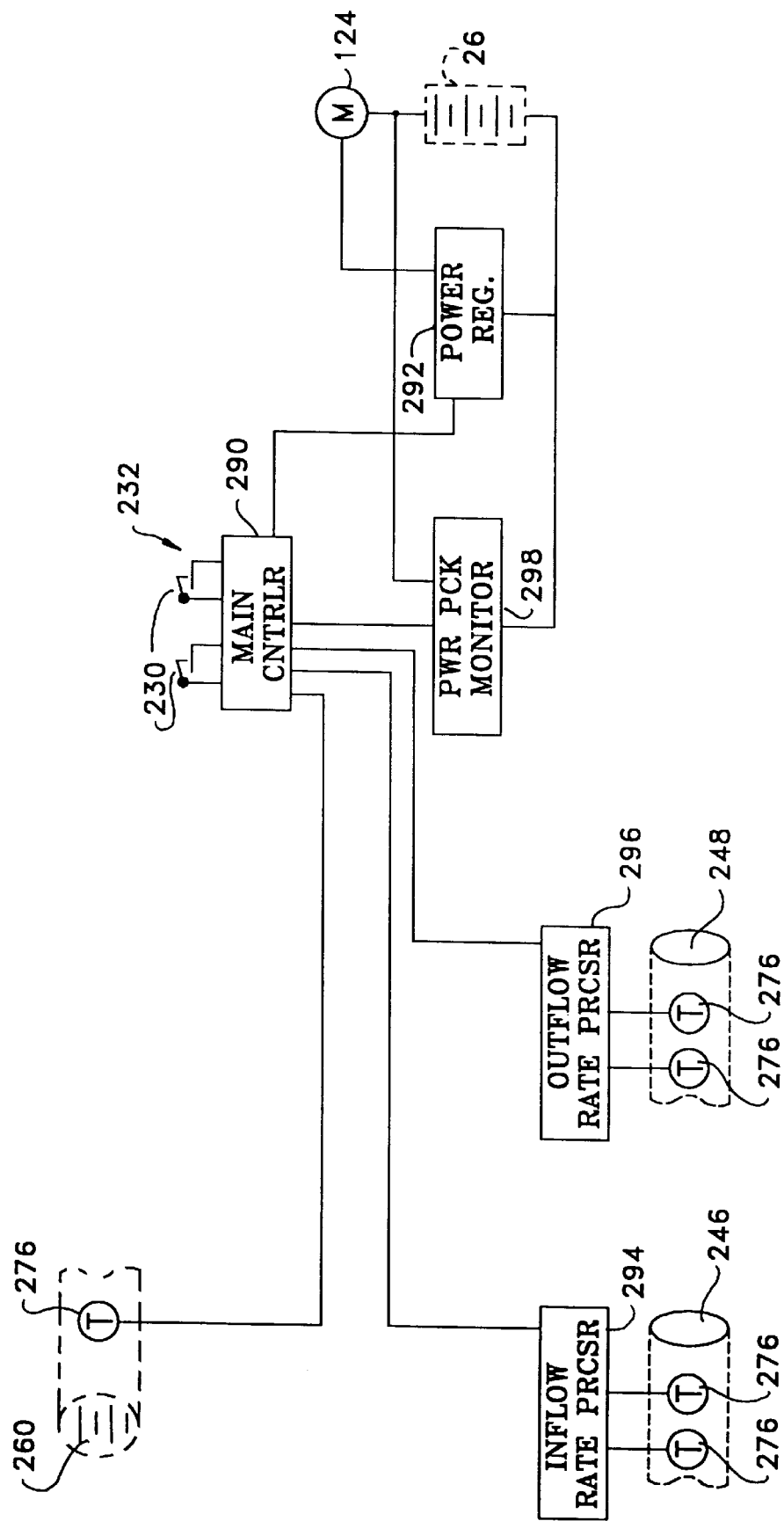
FIG. 18 is a block diagram of the sub-circuits internal the pump control circuit of this invention.

A basic block diagram of the sub-circuits internal to control circuit 232 is shown in FIG. 18. Circuit 232 includes a main controller 290 to which switches 230 are connected. Main controller 290, primarily based on the power level the surgeon sets by selectively closing the switches 230, establishes the level of the power that is to be applied to the motor 124.

Main controller 290 produces a signal representative of the power to be applied to the motor 124. This signal is applied to a power regulator 292. The power regulator 292, based on the signal from main controller 290, regulates the power that is applied from power pack 26 to the motor 124. In the version of the invention depicted in FIG. 18, power regulator 292 performs pulse modulation of a constant voltage signal that is applied to the motor 124. This pulse modulation is performed by selectively tieing the motor 124 to the ground plane internal to the control circuit 232. The connecting of the motor 124 to ground effectively closes the circuit over which power is applied to the motor.

Figure 18A:
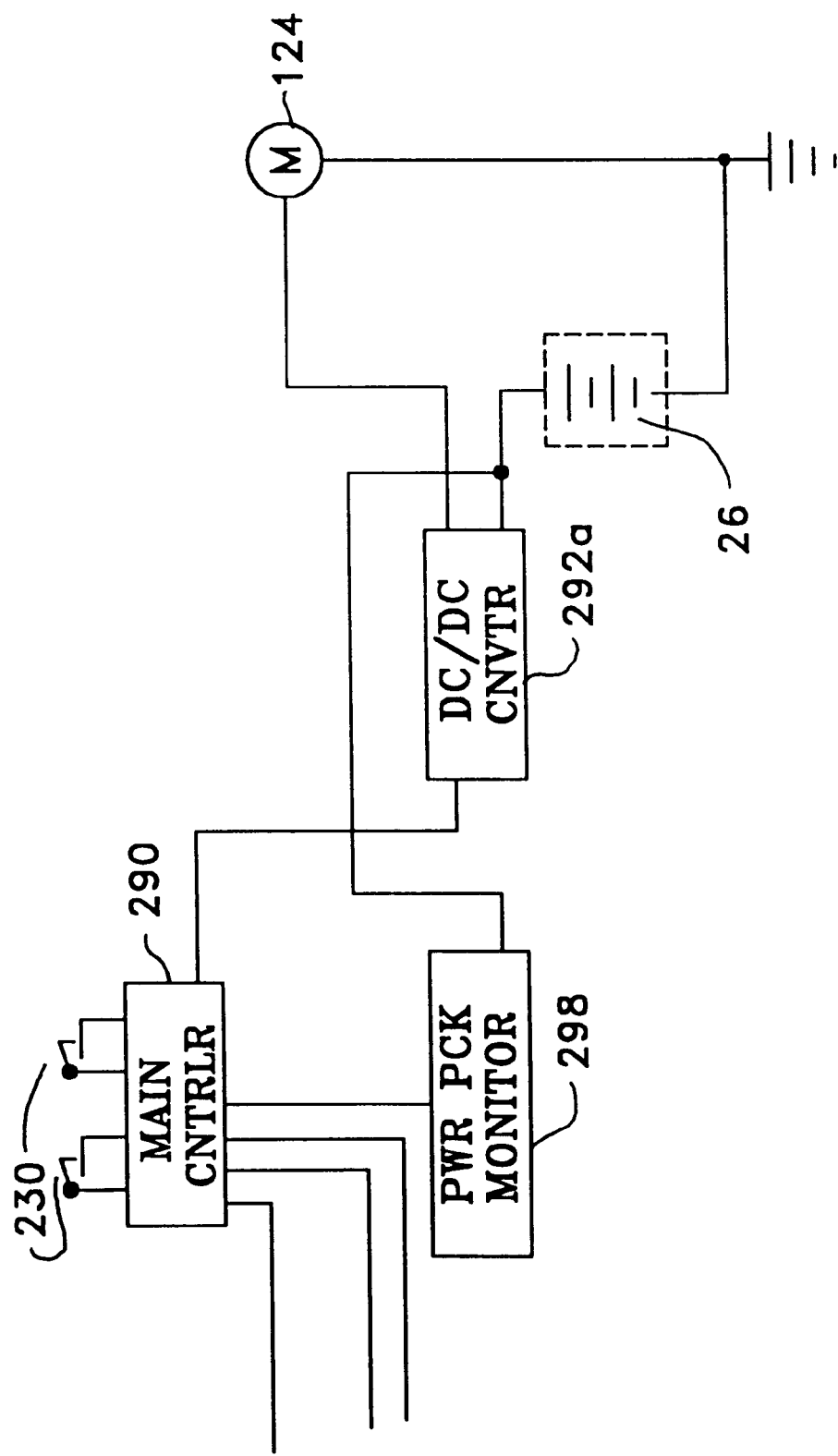
FIG. 18A is a block diagram of an alternative circuit for supplying energization signals to the pump.

In an alternative version of the invention depicted in FIG. 18A, the power regulator is a programmable DC/DC converter 292a. This convertor provides a constant, variable voltage level power signal to the motor 124.

Internal to circuit 232 there are also inflow and outflow flow rate processors 294 and 296, respectively. These processors 294 and 296, which are constructed of analog and/or digital circuit elements, generate signals representative of the rate of flow through chassis tubes 246 and 248, respectively. The inflow processor 294 receives as input signals the pressure signals from transducers 276 integral with tube 246. The outflow processor 296 receives as input signals the pressure signals from the transducers 276 mounted to tube 248. Each flow rate processor 294 and 296 generates signals representative of the rate of fluid flow through the tube with which the processor is associated. These flow rate signals are applied to the main controller 290.

The signal produced by transducer 276 mounted in measurement conduit 260 is applied directly to the main controller 290. It should be understood that the algorithms that main controller 290 employs to regulate the energization of the pump motor 124 are proportional integral differential algorithms. The algorithms are proportional in the sense that changes in the measured fluid state result in a change in the power level of the pump established by the motor controller 290. Integral forms of these signals are used so as to eliminate any short noise spikes in the state signals. Differentiated versions of these integrated signals are employed in that so that main controller 290 not only corrects for changes in the sensed state(s) of the measure fluid, it further corrects based on the rate of change of the sensed fluid state(s).

Control circuit 232 further includes a sub-circuit 298 for measuring the current out of the power pack 26 and the voltage across the power pack. Sub-circuit 298 produces output signals representative of these changes states of the output signal from the power pack 26. The signals produced by sub-circuit 298 are applied to the main controller 290.

The fluid management pump system 20 of this invention provides an irrigation/distention solution to a surgical site. Pump 22 provides the pumping force for forcing the fluid from the supply bags 24 through the inflow tube 28 and cannula 30 to the surgical site. The hand controller 38 regulates the energization of the pump 22 so as to control the rate at which the fluid is forced to the surgical site.

The surgeon sets both the rate at which the solution is followed to the site and the fluid pressure at the site by depressing buttons 42 and 44 and setting flow control valve 46. Specifically, the surgeon raises/lowers the fluid pressure at the surgical site by depressing button 42 or 44 to raise/lower the power applied to the motor 124 while holding the setting of fluid control valve 46 constant. Alternatively, the surgeon increases or decreases the fluid flow rate through the surgical site by resetting the position of fluid control valve 46 without manually changing the power settings by depressing button 42 or 44. In this way, independent control of flow rate and pressure is achieved.

In versions of the invention in which transducers 276 are installed in the hand controller 38, the signals representative of the fluid state generated by the transducers are also used to regulate the application of power to the pump 22. Specifically, if the transducer 276 employed to measure fluid pressure at the surgical site indicates that there has been a drop or a rise in fluid pressure, main controller 290 generates a control signal to cause, respectively, an increase or a decrease in power to the pump.

If the transducers 276 associated with the chassis tube 246 through which the fluid is introduced into the surgical site indicate a drop in fluid flow rate, the main controller 290 increases the power to the pump 22. Executing this adjustment maintains the fluid pressure at the surgical site. If the transducers 276 associated with the chassis tube 248 through which fluid flows from the surgical site indicate that there is a drop in fluid flow, the main controller 290 causes the power to the pump to be decreased. This adjustment also serves to maintain the fluid pressure at the surgical site.

In versions of the invention in which control circuit 232 is provided with power pack state monitoring sub-circuit 298, main controller 290 further adjusts the power applied to the pump 22 as a function of the state of the power pack 26. Specifically, if the current produced by the power pack 26 falls, motor controller 290 resets the power applied to the motor 124 to increase the voltage or increase the percent on-duty cycle for the energization signal. Motor controller 290 also is configured to adjust the energization signal applied to motor 124 based on the state of the voltage across the power pack. If the power pack voltage falls and the power regulator 292 is a pulse width signal controller, motor controller 290 causes regulator to increase the on-duty cycle for the energization signal. If, however, control circuit 232 includes the DC/DC converter 292a, motor controller 290 resets the regular to hold the level of the DC energization signal constant.

Accumulator 29 dampens the flow of solution to the surgical site. Usually, when the pump 22 is actuated, the force of solution forced downstream by the pump is sufficient to hold plunger 214 open. Thus, at these times, solution simply flows through the accumulator 29 downstream through the hand controller 38 and cannula 30 to the surgical site. However, there may be times when the pressure in the joint capsule drastically increases. Once this happens, there may be a back up of fluid in the inflow tube 28. If this back up occurs, the back pressure causes plunge 214 to move towards the inward connector sleeve 208. This action prevents the fluid in the accumulator 29 from continuing to back flow. Thus, the back flowing fluid fills the balloon 198 and the balloon thus expands to receive this fluid. The transducer 276 employed to monitor fluid pressure at the surgical site will, while this action is taking place, generate a signal indicating that this pressure rise is occurring. The main controller 290, based on this signal, reduces or shuts off the power to the pump 22.

Owing to the elastic properties of the accumulator balloon 198, once the back flow ceases, the balloon will contract. The contraction forces the fluid in the balloon 198 out through outflow connector 204 and downstream towards the surgical site. This fluid flow thus serves, for at least a short time period, to maintain the fluid pressure at the surgical site. Once the balloon 198 retracts to its normal size, the fluid pressure at the surgical site may start to fall. This pressure drop is measured by the transducer 276 connected to the pressure measurement tube 48. Upon receiving the signal indicating that this pressure drop has occurred, main controller 290 increases power to the pump 22. The fluid discharged from the pump 22 forces the plunger 214 back to the open state.

The fluid management pump system 20 of this invention is designed so that the power that energizes the pump 22 comes from a portable pack 26 that is integrally attached to the pump. Thus, the system of this invention does not employ a separate console for converting line voltage into a signal suitable for energizing the pump. Thus, the system eliminates the need to bring a separate control console into an operating room where such can device adds to the overall clutter. Moreover, unlike systems that include these control consoles, the energization of this system is not dependent on the availability of a wall-mounted power outlet.

A further benefit of this construction of the invention is that the pump system, from the power pack 26 to the hand controller 38 can be assembled as a single unit and sterilized at the point of manufacture. One using this system does not have to sterilize a stand along control console between uses of the system.

Moreover, still another feature of pump system 20 is that hand controller 38 and associated cable 40 are integral with the inflow and outflow tubes 28 and 34, respectively, through which fluid flows to and from the surgical site. A benefit of this construction is that it does not bring a separate control unit, additional clutter into close proximity to the patient. Moreover, since the hand controller 38 is always attached to the tubes 28 and 34, the surgeon always knows where this unit is. Thus, the time spent reaching for this unit in order to adjust fluid flow rates or pressures is held to a minimum.

Still another feature of the system 20 of this invention is that both cannulae 30 and 32 are designed to minimize the pressure drop of fluid through them. Fluid entering cannula 30 through hose barb 82 and opening 84 initially flows in a circular path around the shaft of the endoscope extending through body center space 88. Owing to the curved walls of cannula body 62 that form center space 88 and the circular profile of the body, this flow develops very little turbulence. Due to the continued introduction of fluid into space, the flow does develop an spiral pattern. Thus, the fluid undergoes a gradual tangential, downward turn. Eventually, the fluid does flow down the cannula shaft 52 in the annular space between the inner wall of the shaft and the outer wall of the endoscope.

Since minimal turbulence develops in the flow through the cannula body 62 and cross sectional flow path through body opening 84 and around center space 88 are substantially identical, there is only a small pressure drop across cannula 30 of this invention. For example, measurements have shown that when there is 1.8 lit/min fluid flow rate through the cannula 30, the pressure drop is only between 0.5 and 1.5 psig. An advantage of this low pressure drop is that it minimizes the pumping power required to force liquid through the cannula. The minimization of this pumping force reduces the amount of current that needs to provided to the pump in order to supply the fluid needed to perform a surgical procedure. This reduction in the amount of current that needs to be supplied to the pump 22 makes it possible for the portable power pack 26 to be able to supply current to the pump for an appreciable length of time.

Cannula 32 is also designed to minimize the pressure drop of the fluid flowing through it. Specifically, fluid flows through shaft 94 head bore 108 and hose barb 106 of cannula 32 along a linear path of travel. Moreover, the flow path through has a cross section area that is essentially constant along the length of the cannula. Also, pressure sampling tube 112 is positioned to be located around the outer perimeter of the flow through space in shaft 94. This arrangement minimizes the development of turbulence as fluid flows around the end of the sampling tube 112. Collectively, these features ensure that for a fluid flowing at a rate of approximately 1.8 lit/min through cannula 32, the pressure drop is less than 1.5 psig.

Still another benefit of cannula 32 is that it is a relatively simple and economic task to permanently weld or otherwise secure the pressure sampling tube 112 to the inside wall of shaft 94. Thus, cannula 32 in addition to serving as low pressure loss conduit for removing fluid from (or introducing fluid into the surgical site) and for extracting a water column for measurement purposes, is relatively inexpensive to manufacture.

There is another benefit associated with the low loss cannulae 30 and 32. Since significant quantities of pressure do not have to be expended forcing fluid through the cannulae 30 and 32, the pump 22 need only be designed to provide a fluid flow that is at a relatively small pressure. For example, in versions of the invention designed to provide fluid at a flow rate of 1.8 lit/min, the pump 22 may be designed to discharge this fluid at a pressure of 10 psig or less. In more preferred versions of the invention, the pump designed to output fluid at the above rate will do so at a maximum pressure of 5 psig. An advantage of this construction of the invention is that, in the event the outflow of fluid from the surgical site is blocked, there is little likelihood that the pump 22 will cause a large build up of fluid pressure that could potentially injure the patient. This benefit of the invention is especially useful in versions of the system 20 that, as discussed below, are not provided with a transducer for measuring fluid pressure at the surgical site.

Still another feature of the system 20 of this invention is that the vanes 182 of the impeller are forward swept. Consequently, when the speed of the pump 22 is increased to increase fluid outflow, the pressure output of the fluid likewise increases.

The pump chassis 122 of this invention is constructed so that integrally formed with the chassis is conduit 174 which is shaped to have a 90° curve. Thus, the solution is discharged from the chassis along a vector that is downwardly directed and parallel to the longitudinal axis of the pump 22. This arrangement minimizes the extent to which the inflow tube 28, upon exiting the pump 22, simply sticks out of the pump. Moreover, since the conduit 174 is formed integrally with the chassis, this structure eliminates the need to provide an additional piece of rigid tubing in order to cause this desired change in flow path. Thus, the pump 22 of this invention has a space efficient and aesthetically pleasing fluid flow path that does not significantly add to the cost of producing the pump.

The accumulator 29 serves as a reservoir for fluid forced through pump when a condition exists in which a back flow could possible. This fluid is stored in the accumulator 29 until this conditions ceases to be present. Once the back flow condition is over, the accumulator forces the fluid downstream to the surgical site. Thus, the accumulator 29 stores the energy previously generated by the pump and releases this energy when needed. The accumulator 29 thus serves to further reduce the amount of energy that needs to be applied to the pump 22 in order to keep this system 20 in operation.

Moreover, even during times when there is no back flow back into the accumulator 29, its body expands and contracts so as with variations in fluid flow so as to minimize drastic pressure changes at the surgical site.

It should be recognized that the foregoing description has been limited to one specific embodiment of the invention. It will be apparent, however, from the description that it can be practiced using other components and with other arrangement than the one that has been described. For example, one need not always employ cannula 30 as the conduit for introducing solution to the surgical site and/or cannula 32 as the conduit through which fluid is discharged from the surgical site. Sometimes, the purposes for which cannulae 30 and 32 are employed may be reversed. When cannula 30 is used as the conduit through which fluid is discharged from the surgical site, the fluid flows up 52 and into body center space 88. The fluid strikes the curved inner wall of body 88 and develops a circular flow around the hub frame 58. After flowing through the center space 88, the fluid is discharged out of the cannula through body opening 84 and hose barb 86. Owing to the curved nature of the flow and the fact that the flow path has an essentially constant cross sectional area, there is again a relatively small pressure drop across this cannula 30 when it is used as a discharge cannula.

It should similarly be understood that, regardless of the direction of fluid flow through cannula 32, the pressure drop across this cannula is relatively low.

Moreover, it should likewise be recognized that the power pack 26 may have other energy providing cells than the described batteries 126. For example, power pack 26 may include NiCad cells that can be repetitively recharged for multiple uses. Alternatively, the power pack may have rechargeable fuel cells. These cells, once the power in them is discharged, are recharged by refueling the chemical solution contained therein with a fresh solution.

It should likewise be recognized that the hand controller 38 and the control circuit 232 may vary from what has been described. Not all controllers may include the transducers for measuring fluid flow through inlet and outlet tubes 28 and 34, respectively, or a transducer for measuring fluid pressure at the surgical site. Similarly, the power pack monitor circuit 298 for measuring current out of and/or voltage across the power pack may likewise be omitted. Thus, in its most basic form, the control circuit 232 may regulate the energization of the motor based only on the depression of buttons 42 and 44.

Similarly, components may be added to the hand controller 38 that are different from the described components. For example, other sensors may be used to measure fluid flow through the inflow and outflow tubes 28 and 34, respectively. Also, a sensor may be provided to monitor the open/close state of fluid control valve 46. In many preferred versions of this invention, this sensor is a variable resistor hat functions as the mounting boss 239. The wiper of this resistor is connected to and set by the rotation of the valve body 234. Alternatively, this sensor could consist of a Hall effect sensor that generates a signal based on the relative position of a magnet mounted in valve body 234. The signal produced by this sensor is applied to the main controller 290. The main controller 290 in turn, regulates the energization of the pump based on the signal representative of the state of the valve. For example, should this signal indicate that degree to which the valve 46 is opened is increased, motor controller 290 will cause the power to the pump to increase in order to maintain fluid pressure.

Alternatively displays may be built into more advance versions of hand controller 38. These displays can provide information regarding the fluid flow rates to and from the surgical site and/or an indication of fluid pressure.

Moreover, in some versions of the invention, control circuit 232 may regulate the open/closed state of the valve. In these versions of the invention, the valve body, or a bushing around the valve, may be formed from material having a very low coefficient of friction such as the Teflon. Also in these versions of the invention, one or more magnets are integrally mounted in the valve body. The portion of chassis 224 in which the valve is seated has plural stators that are actuated so as to cause the movement of the magnets. This movement causes the selected rotation of the valve 46. A stator energization circuit, (not illustrated) under the control of the main controller 290, selectively energizes the stators so as to set the valve in a selected open/closed state.

In these versions of the invention, the surgeon depresses buttons to regulate the fluid pressure developed at the surgical site. As a result of the depression of the buttons, the main controller 290 selectively modulates the power applied to the motor and the open/closed state of the valve 46.

Also, it should be understood that, while for manufacturing efficiencies, it may desirable to place all the components of the control circuit on a single ASIC, that may not always be the case. In some versions of the invention, the control circuit may include plural components.

Moreover, in some versions of the invention, the power regulator circuit may not be integral with the control circuit 232. In these versions of the invention, the power control circuit may be located in the power pack 26 or pump chassis 122. In these versions of the signal, the control signal for regulating the energization signal applied to the motor 124 is generated by the main controller 290 and applied to the power control circuit over one of the conductors internal to cable 40. An advantage of the version of the invention is that it eliminates the need to route the power signal applied to the motor through the hand controller 38. Still another benefit of this version of the invention is that it reduces the number of circuit components that need to be fitted into the hand controller 38.

Therefore, it is the object of the appended claims to cover all such modifications as come within the true spirit and scope of this invention.

What is claimed is:

1. A fluid management pump system for supplying fluid from a container to a surgical site, said system comprising:
    an electrically actuated pump to which fluid from the container is supplied, said pump having an outlet conduit and being configured to force fluid flowed from the container through the outlet conduit;
    a portable power pack connected to said pump for supplying electrical energy to said pump;
    an inflow tube connected to the pump outlet conduit, said inflow tube serving as a conduit over which the fluid discharged from the pump is flowed to the surgical site;
    a cable having first and second ends, the first end of the cable being connected to said pump and said power pack, said cable having wires connected to said pump and said power pack over which signals for regulating the energization of the pump are carried and said cable being attached to said inflow tube;
    an outflow tube through which fluid discharged from the surgical site is drained from the surgical site, said outflow tube being attached at least on partial length thereof to said inflow tube; and
    a hand controller mounted to said inflow tube and said outflow tube, said hand controller including:
        a pump control circuit to which the second end of said cable is connected, said pump control circuit having a used actuated switch for regulating said pump and being configured to generate the signals for regulating the energization of the pump based on the actuation of said switch; and
        an adjustable flow control valve for regulating fluid flow through said outflow tube.

* * * * *